(12) United States Patent
Davis

(10) Patent No.: US 7,081,469 B2
(45) Date of Patent: Jul. 25, 2006

(54) BENZIMIDAZOLE VASCULAR DAMAGING AGENTS

(75) Inventor: Peter David Davis, Watlington (GB)

(73) Assignee: Angiogene Pharmaceuticals Ltd., Oxfordshire (GB)

( * ) Notice: Subject to any disclaimer, the term of this patent is extended or adjusted under 35 U.S.C. 154(b) by 195 days.

(21) Appl. No.: 10/612,163

(22) Filed: Jul. 3, 2003

(65) Prior Publication Data

US 2004/0058972 A1    Mar. 25, 2004

Related U.S. Application Data

(63) Continuation of application No. 09/889,061, filed as application No. PCT/GB00/00099 on Jan. 14, 2000, now Pat. No. 6,645,950.

(30) Foreign Application Priority Data

Jan. 15, 1999    (GB) ................................ 9900752.8

(51) Int. Cl.
*A61K 31/415*    (2006.01)
*A61K 31/165*    (2006.01)
*A61K 31/10*    (2006.01)

(52) U.S. Cl. ...................... 514/388; 514/389; 514/391; 514/394; 514/622; 514/709; 514/708

(58) Field of Classification Search ................ 514/388, 514/389, 391, 394, 622, 709, 708
See application file for complete search history.

(56) References Cited

U.S. PATENT DOCUMENTS

| 3,694,455 A | 9/1972 | Dunn |
| 3,928,375 A | 12/1975 | Diiwel et al. |
| 3,965,113 A | 6/1976 | Beard et al. |
| 3,984,561 A | 10/1976 | Loewe et al. |
| 5,763,473 A | 6/1998 | Elokdah et al. |

FOREIGN PATENT DOCUMENTS

| DE | 2164690 A | 7/1973 |
| DE | 2332343 A | 1/1975 |

OTHER PUBLICATIONS

Nare et al. Biochemical Pharmacology (1994), 48(12), 2215-22.*
Kruse, L.I., et al., "Synthesis, Tubulin Binding, Antineoplastic evaluation, and Structure-Actvity Relationship of Oncodazole Analogues," Journal of Medicinal Chemistry, vol. 32, No. 2, Feb. 1989, pp. 409-417,XP002142971.
Lacey, E., et al., "Activity of Benzimidazole Carbamates Against L1210 mouse Leukaemia cells: Correlation with in Vitro Tubulin Polymerization assay," Biochemical Pharmacology, vol. 34, No. 19, 1985, pp. 3603-3605, XP002056333.
Chemical Abstract of de Brabander, M.J., et al., "The effects of methyl5-(2-thienylcarbonyl)-1H-benzimidazol-2-yl Carbamate. (R 17934: NSC 238159), a new synthetic antitumoral drug interfering with microtubles, on mammalian cells cultured in vitro," p. 26; XP002143095, cited in the application abstract & Cancer Res., vol. 36, No. 3, 1976, pp. 905-916, Chemical Abstract, vol. 84, No. 21.
Khan, A.M. et al., "Studies on enteric anthelmintics: Impact of single point structural change on the activity profile," Zeitschrift Fur Naturfoschung, B, vol. 43, No. 2, Feb. 1988, pp. 233-237.
Raeymaekers, A.H.M., et al., "Synthesis and Anthelmintic Activity of Alkyl-(5-acyl-1H-benzimidazol-2yl) carbamates," Arzneimittel-Forschung, vol. 28 (I), No. 4, 1978, pp. 586-594, XP002142973.
Abuzar, S., et al., "Synthesis and anthelmintic activity of 2,2'-disubstitued 5,5-dibenzimidazolylsufides and sulfones," Arzeimittel-forschung, vol. 36 (I), No. 3, Mar. 1986, pp. 416-419, XP002142974.
Database Crossfire "Online", Beilstein Institut zur Foerderung der Chemischen Wissenschaften; XP 002142975, Beilstein Registry No. 4595458 & Indian J. Chem. Sect. B, vol. 19, No. 7, 1980, pp. 536-538.
Database Crossfire "Online" Beilstein Institut zur Foerderung der Chemischen Wissenschaften; XP 002142976, Beilstein Registry No. 5651135 & Indian J Chem. Sect. B, vol. 24, 1985, pp. 754-760.
Database Crossfire "Online" Beilstein Institut zur Foerderung der Chemischen Wissenschaften; XP002142977, Beilstein Registry No. 5622648 & Indian J. Chem. Sect. B, vol. 24, 1985, pp. 747-753.

(Continued)

*Primary Examiner*—Sheng Jun Wang
*Assistant Examiner*—Jennifer Kim
(74) *Attorney, Agent, or Firm*—Gilberto M. Villacorta; Matthew E. Mulkeen; Foley & Lardner LLP

(57) ABSTRACT

Vascular damaging agents composed of substituted 5(6)-substituted benzimidazole-2-carbamates are provided. These agents are useful in the preparation of medicaments for the treatment of diseases involving neovascularisation, particularly for the treatment of solid tumors, macular degeneration, diabetic retinopathy, rheumatoid arthritis, psoriasis, and atherosclerosis. Embodiments include a 5(6)-substituted benzimidazole-2-carbamate of formula I

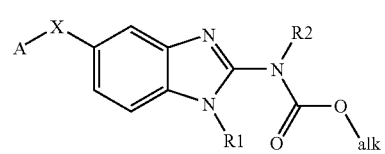

wherein A represents a multi-substituted alkyl group or aromatic ring.

14 Claims, No Drawings

OTHER PUBLICATIONS

Database Crossfire "Online" Beilstein Institut zur Foerderung der Chemischen Wissenschaften; XP 002142978, Beilstein Registry No. 5669479, 5670801, 5667941, 5667940, 5665325 & Indian J. Chem. Sect. B, vol. 24, 1985, pp. 730-732.

Database Crossfire "Online" Beilstein Institut zur Foerderung der Chemischen Wissenschaften; XP 002142978, Beilstein Registry No. 4615289, 4609187, & Indian J. Chem. Sect. B, vol. 23, No. 12, 1984, pp. 1274-1278.

Database Crossfire "Online" Beilstein Institut zur Foerderung der Chemischen Wissenschaften; XP 002142980, Beilstein Registry No. 6009722, 6007941, 6007769 & Indian J. Chem. Sect. B, vol. 24, 1985, pp. 178-181.

* cited by examiner

BENZIMIDAZOLE VASCULAR DAMAGING AGENTS

This application is a continuation of U.S. application Ser. No. 09/889,061, filed Oct. 22, 2001, now U.S. Pat. No. 6,645,950 which is a national phase application under 35 U.S.C. § 371 of PCT/GB00/00099 filed Jan. 14, 2000, which claims priority from GB serial number 9900752.8, filed Jan. 15, 1999.

This invention relates to vascular damaging agents and particularly to the use of new and known substituted benzimidazoles in the preparation of medicaments for the treatment of diseases involving neovascularisation.

Formation of new vasculature by angiogenesis is a key pathological feature of several diseases (J Folkman, New England Journal of Medicine 333, 1757–1763 (1995)). For example, for a solid tumour to grow it must develop its own blood supply upon which it depends critically for the provision of oxygen and nutrients; if this blood supply is mechanically shut off the tumour undergoes necrotic death. Neovascularisation is also a clinical feature of skin lesions in psoriasis, of the invasive pannus in the joints of rheumatoid arthritis patients and of atherosclerotic plaques. Retinal neovascularisation is pathological in macular degeneration and in diabetic retinopathy. In all these diseases reversal of neovascularisation by damaging the newly-formed vascular endothelium is expected to have a beneficial therapeutic effect.

5(6)-Substituted benzimidazole-carbamates are known and have found use as antiparasitic agents (P. J. Islip in Burgers Medicinal Chemistry (M. E. Wolff ed.), Fourth Edition, Part II, p 481, (1979)). Examples of such compounds include mebendazole, fenbendazole, oxibendazole, flubendazole, albendazole, cyclobendazole, parbendazole, dribendazole, luxabendazole, and etibendazole. Their mode of action for their antiparasitic action is believed to involve selective binding to tubulin of the target parasite while having little effect due to binding tubulin of the mammalian host (Biochim. Biophys. Acta 630, 271–278, (1980)). Some of these compounds have been shown to be antimitotic for cancer cells and one particular 5(6)-substituted benzimidazole-2-carbamate, nocodazole, has therefore been studied as an anticancer agent (Cancer Research, 36, 905–916 (1976)). No effects on neovasculature have been reported for any of these compounds.

Some structurally-unrelated compounds which bind tubulin have been shown to have anti-vascular effects when given at their maximum tolerated dose (MTD) (S. A. Hill et al. Eur. J Cancer, 29A, 1320–1324 (1993)) but other tubulin-binding agents, such as docetaxel, have no vascular-damaging activity even when administered at the MTD. The presence of tubulin-binding properties is then not predictive for antivascular activity.

According to the present invention there is provided the use of 5(6)-substituted benzimidazole-2-carbamates for the preparation of compositions for the treatment of diseases involving angiogenesis in which the 5(6)-substituted benzimidazole carbamate has the formula

I

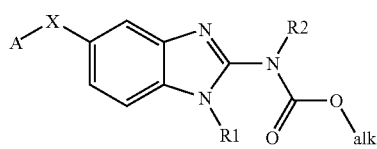

wherein
Alk is an alkyl group

X is oxygen, sulphur, sulphinyl, sulphonyl, carbonyl (CO), thiocarbonyl (CS), sulphonyloxy, NH, iminomethylene (C=NH), N-hydroxyiminomethylene, N-alkoxyiminomethylene, dialkoxymethylene, 1,3-dioxolan-2yl, 1,1-ethenyl, a group $CHR^3$ or a bond $R^1$ is hydrogen, alkylaminocarbonyl or alkoxycarbonyl $R^2$ is hydrogen, alkoxycarbonyl, cyanomethyl, cyanoethyl, alkoxymethyl or acetoxymethyl.

$R^3$ is hydrogen, hydroxy, alkoxy or amino

A is an optionally substituted aromatic, optionally substituted heteroaromatic, optionally substituted heterocycloalkyl, optionally substituted alkyl or optionally substituted cycloalkyl group and the pharmaceutically acceptable salts, solvates and hydrates thereof.

Particular substituents that may be present on the group A include one or more substituents selected from a group Y, optionally substituted alkyl,(where substituents on such alkyl group may include one or more selected from hydroxy, amino, alkylamino, dialkylamino, halogen, carboxyl, $SO_3H$, sulphate, phosphate, alkoxycarbonyl, aralkoxycarbonyl, alkoxycarbonylamino, aminoalkylaminocarbonyl and cyano), halogen, hydroxy, amino, alkoxy, alkylthio, cyano, nitro, sulphate, isothiocyanate, aryl, heteroaryl and heterocycloalkyl.

Y is a group selected from phosphate, alkylphosphate, $C(O)R^4$, $OC(O)R^4$, $SO_2R^4$, $NHC(O)R^4$, $NR^5C(O)R^4$, $SR^4$, $S(O)R^4$, $OSO_2R^4$, $NHSO_2R^4$, $NR^5SO_2R^4$, $SO_3H$, $CO_2H$ and $CO_2R^5$ where $R^4$ is a group selected from hydrogen, $R^5$, $OR^5$, $NHR^5$, $NR^5R^6$, aryl, heteroaryl or heterocycloalkyl such aryl, heteroaryl or heterocycloalkyl groups being optionally substituted with one or more substituents selected from alkyl, heterocycloalkyl, haloalkyl, hydroxy, nitro, cyano, amino, alkylamino, dialkylamino, halogen, carboxyl, $SO_3H$, sulphate and phosphate. $R^5$ and $R^6$, which may be the same or different, are each an alkyl group optionally substituted with one or more substituents selected from hydroxy, amino, alkylamino, dialkylamino, guanidino, halogen, carboxyl, $SO_3H$, sulphate, phosphate, aryl and heteroaryl.

Some of the compounds usable in the invention are known, for example the following compounds within the following formula:

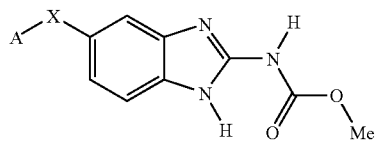

These compounds are

|  | X | A |
|---|---|---|
| Fenbendazole | S | Ph |
| Mebendazole | CO | Ph |
| Albendazole | S | nPr |
| Oxibendazole | O | nPr |
| Nocodazole | CO | 2-thienyl |

Certain of these compounds are novel. In one embodiment the novel compounds are those of formula I in which at least one of the substituents on the group A is a group Y where Y is as hereinbefore defined. Particularly preferred are compounds defined by the formula

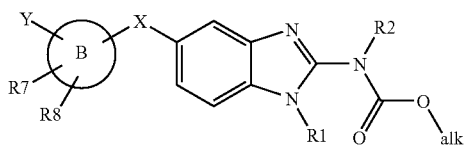

wherein
alk is an alkyl group
B is an aromatic or heteroaromatic ring
X is oxygen, sulphur, sulphinyl, sulphonyl, carbonyl (CO), thiocarbonyl (CS), sulphonyloxy, NH, iminomethylene (C=NH), N-hydroxyiminomethylene, N-alkoxyiminomethylene, dialkoxymethylene, 1,3-dioxolan-2yl, 1,1-ethenyl, a group $CHR^3$ or a bond
$R^1$ is hydrogen, alkylaminocarbonyl or alkoxycarbonyl
$R^2$ is hydrogen, alkoxycarbonyl, cyanomethyl, cyanoethyl, alkoxymethyl or acetoxymethyl
$R^3$ is hydrogen, hydroxy, alkoxy or amino
Y is as hereinbefore defined
$R^7$ and $R^8$ are each independently H, alkyl, halogen, hydroxy, amino, alkylamino, dialkylamino, alkoxy, alkylthio, cyano, nitro, or trifluoromethyl with the proviso that Y is not NHC(O)Me and when B is a thiophene ring then Y is not $C(O)CF_3$ and when B is a 5(6)-benzimidazole ring then Y is not $NHCO_2Me$ or $NHCO_2Et$ and the pharmaceutically acceptable salts, solvates, hydrates and prodrugs thereof As used herein the term "alkyl", alone or in combinations, means a straight or branched-chain alkyl group containing from one to seven, preferably a maximum of four, carbon atoms such as methyl, ethyl, propyl, isopropyl, butyl, sec-butyl, t-butyl and pentyl. Examples of alkoxy groups are methoxy, ethoxy, propoxy, isopropoxy, butoxy and t-butoxy. The term "halogen" means fluorine, chlorine, bromine or iodine.

The term "aryl" as used herein unless otherwise stated includes reference to a $C_{6-10}$ aryl group which may, if desired, carry one or more substituents selected from halogeno, alkyl, haloalkyl, alkoxy, hydroxy, amino, nitro and cyano. The term "aralkoxy" means an alkoxy group substituted with an aryl group.

The term heteroaryl is defined herein as a mono- or bi-cyclic aromatic group containing one to four heteroatoms selected in any combination from N, S or O atoms and a maximum of 9 carbon atoms. Examples of heteroaryl groups include pyridyl, pyrimidyl, furyl, thienyl, pyrrolyl, pyrazolyl, indolyl, benzofuryl, benzothienyl, benzothiazolyl, oxazolyl, isoxazolyl, thiazolyl, isothiazolyl, imidazolyl, triazolyl, quinolyl and isoquinolyl groups.

The term heterocycloalkyl includes heterocycloalkyl groups containing 3–6 carbon atoms and one or two oxygen, sulphur or nitrogen atoms. Particular examples of such groups include azetidinyl, pyrrolidinyl, piperidinyl, homopiperidinyl, piperazinyl, homopiperazinyl, morpholinyl or thiomorpholinyl groups.

The term cycloalkyl means a cycloaliphatic group containing 3–10 carbon atoms such as, for example, cyclopropyl, cyclobutyl, cyclopentyl or cyclohexyl.

One particularly preferred group of compounds are those of formula II in which Y is a phosphate group.

Another particularly preferred group of compounds are those of formula II in which Y is a group $NR^5C(O)R^4$, $R^5$ is hydrogen and $R^4$ is a 1-aminoalkyl group which can be further substituted for example by a hydroxy group.

Where one or more functional groups in compounds of formula I or II are sufficiently basic or acidic the formation of salts is possible. Suitable salts include pharmaceutically acceptable salts for example acid addition salts including hydrochlorides, hydrobromides, phosphates, sulphates, hydrogen sulphates, alkylsulphonates, arylsulphonates, acetates, benzoates, citrates, maleates, fumarates, succinates, lactates and tartrates, salts derived from inorganic bases including alkali metal salts such as sodium or potassium salts, alkaline earth metal salts such as magnesium or calcium salts, and salts derived from organic amines such as morpholine, piperidine or dimethylamine salts.

Those skilled in the art will recognise that compounds of formulae I and II may exist as stereoisomers and/or geometrical isomers and accordingly the present invention includes all such isomers and mixtures thereof. The substituted benzimidazole group is capable of existing in tautomeric forms and the formulae I and II are intended to represent all tautomeric forms and the substituent AX- is in the 5(6) position.

Compounds of Formula I or II may be prepared by any process known to a person skilled in the art. Compounds of Formula I or II may be prepared by a number of processes as generally described below and more specifically in the Examples hereinafter. In the following process description, the symbols A, X and alk when used in the formulae depicted are to be understood to represent those groups described above in relation to formula I or II unless otherwise indicated. In the schemes described below it may be necessary to employ protecting groups which are then removed during the final stages of the synthesis. The appropriate use of such protecting groups and processes for their removal will be readily apparent to those skilled in the art.

Thus according to a further aspect of the invention compounds of formulae I and II in which $R^1$ and $R^2$ are hydrogen may be prepared by treatment of a diamine of formula III with a 1,3-bis(alkoxycarbonyl)-S-alkyl isothiourea, for example 1,3-bis(methoxycarbonyl)-S-methyl isothiourea or 1,3-bis(ethoxycarbonyl)-S-methyl isothiourea, in a solvent such as an alcohol, for example methanol or ethanol, optionally mixed with water, at from about room temperature to the reflux temperature of the solvent for about 5 minutes to 6 hours. The reaction medium is preferably made acidic by the addition of for example an organic acid such as acetic acid or p-toluenesulphonic acid.

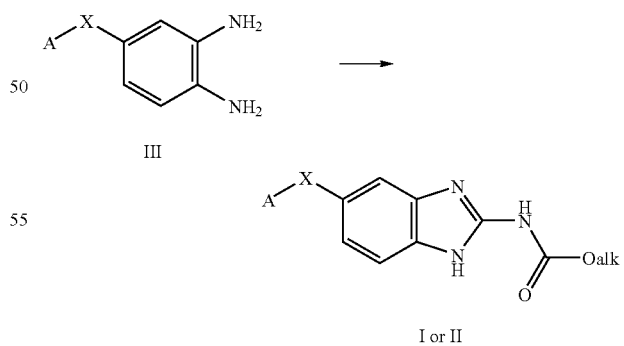

Compounds of formula III are either known or can be prepared by conventional procedures.

Compounds of formulae I and II can also be prepared from other compounds of formulae I and II by chemical modification. Example of such chemical modifications that may be applied are standard alkylation, acylation, reduction, oxidation, sulphation, aromatic halogenation, aromatic nitration, phosphorylation, hydrolysis, condensation, cleavage and coupling reactions. These reactions may be used to add new substituents, to modify existing substituents or to modify other parts of the molecule.

Thus for example a compound of formula I or II in which $R^1$ is hydrogen can be converted into the corresponding compounds where $R^1$ is alkylaminocarbonyl by treatment with an alkyl isocyanate in a solvent such as tetrahydrofuran at a temperature in the range 0° to 40° C., typically room temperature.

In another general example a thioether group in a compound of formula I or II can be converted into a sulphinyl group by treatment with periodate in an aqueous alcohol solvent such as aqueous methanol or in aqeuous acetonitrile at about −20° to 50° C., for about 1 to 16 h. Alternatively this conversion can be effected by treatment with one equivalent of a peracid such as 3-chloroperbenzoic acid in a chlorinated solvent such as dichloromethane or chloroform, at a temperature of about −30° C. to room temperature.

In a further general example a thioether group in a compound of formula I or II can be converted into a sulphonyl group by treatment with two or more equivalents of a peracid such as 3-chloroperbenzoic acid in a chlorinated solvent such as dichloromethane or chloroform, at a temperature of about −30° C. to room temperature.

In a further general example a keto group in a compound of formula I or II can be converted into a carbinol group by treatment with a reducing agent for example a hydride such as lithium aluminium hydride in an ether solvent such as diethyl ether or tetrahydrofuran at a temperature of from about 0° to the reflux temperature of the solvent.

In a further general example a keto group in a compound of formula I or II can be converted into an imine by treatment with ammonia in an alcoholic solvent such as ethanol at around room temperature for an extended period, for example three weeks.

In a further general example a keto group in a compound of formula I or II can be converted into an oxime by treatment with hydroxylamine in an alcoholic solvent such as ethanol at around room temperature to around the reflux temperature of the solvent.

In a further general example a compound of formula I or II containing a hydroxy group can be converted into the corresponding dihydrogenphosphate ester by treatment with for example di-tert-butyl diethylphosphoramidite in the presence of a suitable catalyst for example tetrazole in a solvent such as an ether solvent for example tetrahydrofuran at a temperature in the range −40 to 40° C., conveniently at or near room temperature, followed by treatment with an oxidising agent for example 3-chloroperoxy benzoic acid or magnesium monoperoxyphthalate at a temperature in the range −78° C. to 40° C. preferably −65 to −10° C. The resulting intermediate phosphate triester is treated with an acid for example trifluoroacetic acid in a solvent such as a chlorinated solvent e.g. dichloromethane at a temperature in the range −30 to 40° C. conveniently at or near 0° C. to give the compound of formula I or II containing a dihydrogenphosphate ester.

In another general example an O-alkyl group may be cleaved to the corresponding alcohol (OH) by reaction with boron tribromide in a solvent such as a chlorinated solvent e.g. dichloromethane at a low temperature e.g. around −78° C.

In a further general example compounds of formula I or II may be alkylated by reaction with a suitable alkylating agent such as an alkyl halide, an alkyl toluenesulphonate, an alkyl methanesulphonate or an alkyl triflate. The alkylation reaction can be carried out in the presence of a base for example an inorganic base such as a carbonate e.g. caesium or potassium carbonate, a hydride such as sodium hydride or an alkoxide such as potassium t-butoxide in a suitable solvent such as an aprotic solvent e.g. dimethylformamide or an ether solvent such as tetrahydrofuran at a temperature of around −10 to 80° C.

In a further general example compounds of formula I or II containing an amine group may be acylated by treatment with a carboxylic acid and a coupling reagent, for example dicyclohexylcarbodiimide, in a sutable solvent for example an aprotic solvent such as dimethylformamide, an ether solvent such as tetrahydrofuran, a chlorinated solvent for example dichloromethane or a solvent mixture at a temperature in the range 0° to 60°, preferably about room temperature.

In a further general example a compound of formula I or II containing an OH group can be converted into a carbamate by reaction with an alkyl isocyanate or a carbamoyl chloride in an aprotic solvent such as dimethylformamide, an ether solvent such as tetrahydrofuran, a chlorinated solvent for example dichloromethane or a solvent mixture in the presence of a base such as a tertiary amine base for example triethylamine at a temperature in the range −20° to the reflux temperature of the solvent, conveniently at or around room temperature.

In a further general example a compound of formula I or II containing an amino group can be converted into a urea by reaction with an isocyanate or a carbamoyl chloride in an aprotic solvent such as dimethylformamide, an ether solvent such as tetrahydrofuran, a chlorinated solvent for example dichloromethane or a solvent mixture in the presence of a base such as a tertiary amine base for example triethylamine at a temperature in the range −20° C. to the reflux temperature of the solvent, conveniently at or around room temperature.

In a further general example a compound of formula I or II containing a hydroxy group can be converted into a carbonate by reaction with an chloroformate in an aprotic solvent such as dimethylformamide, an ether solvent such as tetrahydrofuran, a chlorinated solvent for example dichloromethane or a solvent mixture in the presence of a base such as a tertiary amine base for example triethylamine at a temperature in the range −20° C. to the reflux temperature of the solvent, preferably at or around 0° C.

Preparation of a compound of formula I or II as a single enantiomer or, where appropriate, diastereomer may be effected by synthesis from an enantiomerically pure starting material or intermediate or by resolution of the final product in a conventional manner.

Acid addition salts of the compounds of formula I or II are prepared in a conventional manner by treating a solution or suspension of the free base I or II with about one equivalent of a pharmaceutically acceptable acid. Salts of compounds of formula I or II derived from inorganic or organic bases are prepared in a conventional manner by treating a solution or suspension of the free acid I or II with about one equivalent of a pharmaceutically acceptable organic or inorganic base. Alternatively both acid addition salts and salts derived from bases may be prepared by treatment of the parent compound with the appropriate ion-exchange resin in a standard fashion. Conventional concentration and recrystallisation techniques are employed in isolating the salts.

Compounds according to the invention are able to destroy vasculature that has been newly formed, for example tumour vasculature, while leaving unaffected normal, mature vasculature. The ability of the compounds to act in this way may be determined by the tests described hereinafter.

The compounds according to the invention are thus of particular use in the prophylaxis and treatment of cancers involving solid tumours and in the prophylaxis and treatment of diseases where inappropriate angiogenesis occurs such as diabetic retinopathy, psoriasis, rheumatoid arthritis, atherosclerosis and macular degeneration.

The compounds of the invention may be administered as a sole therapy or in combination with other treatments. For the treatment of solid tumours compounds of the invention may be administered in combination with radiotherapy or in combination with other anti-tumour substances for example those selected from mitotic inhibitors, for example vinblastine, paclitaxel and docetaxel; alkylating agents, for example cisplatin, carboplatin and cyclophosphamide; antimetabolites, for example 5-fluorouracil, cytosine arabinoside and hydroxyurea; intercalating agents for example adriamycin and bleomycin; enzymes, for example aspariginase; topoisomerase inhibitors for example etoposide, topotecan and irinotecan; thymidylate synthase inhibitors for example raltitrexed; biological response modifiers for example interferon; antibodies for example edrecolomab and antibodies against the EGFr, HER2 receptor or VEGF receptor: and anti-hormones for example tamoxifen. Such combination treatment may involve simultaneous or sequential application of the individual components of the treatment.

For the prophylaxis and treatment of disease the compounds according to the invention may be administered as pharmaceutical compositions selected with regard to the intended route of administration and standard pharmaceutical practice. Such pharmaceutical compositions may take a form suitable for oral, buccal, nasal, topical, rectal or parenteral administration and may be prepared in a conventional manner using conventional excipients. For example for oral administration the pharmaceutical compositions may take the form of tablets or capsules. For nasal administration or administration by inhalation the compounds may be conveniently delivered as a powder or in solution. Topical administration may be as an ointment or cream and rectal administration may be as a suppository. For parenteral injection (including intravenous, subcutaneous, intramuscular, intravascular or infusion) the composition may take the form of, for example, a sterile solution, suspension or emulsion.

The dose of a compound of the invention required for the prophylaxis or treatment of a particular condition will vary depending on the compound chosen, the route of administration, the form and severity of the condition and whether the compound is to be administered alone or in combination with another drug. Thus the precise dose will be determined by the administering physician but in general daily dosages may be in the range 0.001 to 100 mg/kg preferably 0.1 to 50 mg/kg.

Biological Activity

The following test was used to demonstrate the activity and selectivity of compounds according to the invention.

Activity Against Tumour Vasculature Measured by Fluorescent Dye.

The following experiment demonstrates the ability of the compounds to damage tumour vasculature.

Tumour functional vascular volume in CaNT tumour-bearing mice was measured using the fluorescent dye Hoechst 33342 according to the method of Smith et al (Brit J Cancer 57, 247–253, 1988). The fluorescent dye was dissolved in saline at 6.25 mg/ml and injected intravenously at 10 mg/kg 6 hours or 24 hours after intraperitoneal drug treatment. One minute later, animals were killed and tumours excised and frozen; 10 μm sections were cut at 3 different levels and observed under UV illumination using an Olympus microscope equipped with epifluorescence. Blood vessels were identified by their fluorescent outlines and vascular volume was quantified using a point scoring system based on that described by Chalkley, (J Natl Cancer Inst, 4, 47–53, 1943). All estimates were based on counting a minimum of 100 fields from sections cut at the 3 different levels. Results are expressed as percentage reduction in vascular volume compared to control.

The activity of compounds of the invention in this assay is shown in Table 1.

TABLE 1

Reduction in tumour vascular volume measured by flourescent dye

| Compound | Dose (mg/kg) (i.p.) | Time (h) | % Reduction in vascular volume |
| --- | --- | --- | --- |
| Fenbendazole | 500 | 6 | 44 |
| Mebendazole | 500 | 6 | 56 |
| Albendazole | 500 | 6 | 51 |
| Oxibendazole | 100 | 6 | 43 |
| Nocodazole | 100 | 24 | 23 |
| Compound of Example: | | | |
| 1 | 500 | 6 | 81 |
| 2 | 500 | 6 | 80 |
| 3 | 50 | 24 | 22 |
| 4 | 50 | 24 | 53 |
| 5 | 50 | 24 | 99 |
| 12 | 50 | 24 | 51 |
| 14 | 50 | 24 | 39 |
| 15 | 50 | 24 | 61 |
| 16 | 50 | 24 | 56 |
| 17 | 50 | 24 | 62 |
| 18 | 50 | 24 | 47 |
| 19 | 50 | 24 | 88 |
| 20 | 50 | 24 | 69 |
| 21 | 50 | 24 | 74 |

The following non-limiting Examples illustrate the invention:

EXAMPLE 1

Methyl [5(6)-(4-hydroxybenzoyl)-1H-benzimidazol-2yl]carbamate

A solution of 3,4-diamino-4'-hydroxybenzophenone (49.6 mg, 0.21 mmol) and 1,3-bis(methoxycarbonyl)-S-methyl isothiourea (98 mg, 0.44 mmol) in ethanol (2.5 ml) was treated with p-toluenesulphonic acid (7 mg) and the mixture heated at reflux for 10 minutes. The mixture was cooled and the precipitate collected by filtration and washed with ethanol and hexane to give the title compound (16 mg) as a white solid m.p. >258° C., $^1$H-NMR (400 MHz, d6-DMSO) δ 7.80 (s, 1H), 7.65 (d, 2H, J=8 Hz), 7.50 (s, 1H), 7.49 (s, 1H), 6.89 (d, 2H, J=8 Hz), 3.77 (s, 3H) ppm. m/e 311 (M+). Anal. Calculated for C16H13N3O4: C, 61.73; H, 4.21; N, 13.49. Found: C, 61.68; H, 4.18; N, 13.36.

EXAMPLE 2

Methyl [5(6)-(4-phosphonooxybenzoyl)-1H-benzimidazol-2yl]carbamate

A solution of methyl [5-(4-(di-tert-butylphosphonooxy) benzoyl)-1H-benzimidazol-2yl]carbamate (1.5 g, 3.0 mmol)

in dichloromethane (55 ml) was cooled in an ice bath and treated with trifluoroacetic acid (6 ml) dropwise. The mixture was allowed to warm to room temperature and stirred for 1 hour before solvents were removed under reduced pressure. The residue was triturated with ether to give the title compound (1.13 g) as a white solid m.p. >258° C., $^1$H-NMR (300 MHz, d6DMSO) δ: 7.84 (s, 1H), 7.75 (d, 1H, J=9 Hz), 7.57 (d, 1H, J=8 Hz), 7.52 (d, J=8 Hz), 7.33 (d, 1H, J=9 Hz), 3.78 (s, 3H) ppm.

The methyl [5(6)-(4-(di-tert-butylphosphonooxy)benzoyl)-1H-benzimidazol-2yl]carbamate used as starting material was prepared as follows:

A solution of methyl [5(6)-(4-hydroxybenzoyl)-1H-benzimidazol-2yl]carbamate (100 mg, 0.3 mmol) in anhydrous tetrahydrofuran (1 ml) stirred under a nitrogen atmosphere was treated with di-tert-butyl diethylphosphoramidite (74 mg, 0.29 mmol) and 1H-tetrazole (54 mg, 0.78 mmol) and the mixture stirred until the reaction was shown to be complete by TLC (about 1 h). The cooled (−40° C.) mixture was treated with 3-chloroperbenzoic acid (79 mg, 0.39 mmol) in dichloromethane (1 ml) and stirred 10 minutes before being allowed to warm to room temperature. The mixture was washed with saturated aqueous sodium bicarbonate followed by brine and the dried (MgSO4) organic phase concentrated under reduced pressure. The residue was chromatographed on silica gel eluting first with 4% methanol/dichloromethane then with 5% methanol/dichloromethane. Methyl [5(6)-(4-(di-tert-butylphosphonooxy)benzoyl)-1H-benzimidazol-2yl]carbamate (35 mg) was obtained as a white solid m.p. 99–101° C.

EXAMPLE 3

Methyl [5(6)-(4-phosphonooxyphenylthio)-1H-benzimidazol-2yl]carbamate

A solution of methyl [5(6)-(4-(di-ter-butylphosphonooxy)phenylthio)-1H-benzimidazol-2yl]carbamate (180 mg) in anhydrous dichloromethane (10 ml) at 4° C. was treated with trifluoroacetic acid (1 ml) and stirred for 1.5 h. The mixture was allowed to warm to room temperature and concentrated under reduced pressure. Ethyl acetate was added and the mixture concentrated again. The residue was triturated with diethyl ether, washed with diethyl ether followed by acetone/water 9:1 and dried to give the title compound (134 mg) as a white solid m.p. 190–193° C. Anal. Calculated for $C_{15}H_{14}N_3O_6PS.3H_2O$: C, 40.1; H, 4.5; N, 9.3. Found: C, 40.1; H, 3.9; N, 9.2.

The methyl [5(6)-(4-(di-tert-butylphosphonooxy)phenylthio)-1H-benzimidazol-2yl]carbamate used as starting material was prepared as follows:

A solution of methyl [5-(4-hydroxyphenylthio)-1H-benzimidazol-2yl]carbamate (200 mg) in a mixture of anhydrous dimethylformamide (2 ml) and anhydrous tetrahydrofuran (2 ml) was treated with di-tert-butyl diethylphosphoramidite (350 mg) and the mixture stirred for 48 h at room temperature. The mixture was cooled to −65° C. and treated gradually with magnesium monoperoxyphthalate (850 mg) so that the temperature remained below −50° C. A saturated aqueous solution of sodium bicarbonate was added, keeping the temperature below −40° C. during the addition then allowing the mixture to warm to room temperature. The mixture was extracted with three portions (50 ml each) of ethyl acetate and the combined extracts washed with brine (50 ml), dried (MgSO4) and concentrated under reduced pressure. The residue was purified by radial chromatography on silica gel eluting with dichloromethane/methanol 9:1 to give methyl [5(6)-(4-(di-tert-butylphosphonooxy)phenylthio)-1H-benzimidazol-2yl]carbamate (180 mg) as a white foam.

EXAMPLE 4

Methyl [5(6)-(4-aminophenylthio)-1H-benzimidazol-2yl]carbamate

Methyl [5(6)-(4-(acetylamino)phenylthio)-1H-benzimidazol-2yl]carbamate (602 mg, 1.78 mmol) was dissolved in mixture of methanol (24 ml) and hydrochloric acid (10%, 6 ml) and heated under reflux for 16 h. The solution was neutralised with ammonia solution and the methanol removed under reduced pressure. The white precipitate was collected by filtration, washed with water and dried in vacuo to give 392 mg of a pale yellow solid m.p. 282–284° C. m/e 298 (M$^+$).

EXAMPLE 5

Methyl [5(6)-(4-alanylaminophenylthio)-1H-benzimidazol-2yl]carbamate

A suspension of methyl [5(6)-(4-(Nα-tert-butoxycarbonylalanylamino)phenylthio)-1H-benzimidazol-2yl]carbamate (250 mg) in dichloromethane (20 ml) was treated with trifluoroacetic acid (4 ml). The mixture was allowed to warm to room temperature and concentrated under reduced pressure. Ethyl acetate was added and the mixture concentrated again. The residue was triturated with diethyl ether to afford the trifluoroacetic acid salt of the title compound (105 mg) as a white solid m.p. 178–182° C. m/e 485 (M+). Anal. Calculated for $C_{18}H_{19}N_5O_3S.2C_2HF_3O_2$ C, 43.1; H, 3.5; N, 11.4. Found C; 42.8; H, 3.8; N, 11.3

The methyl [5(6)(4-(Nα-tert-butoxycarbonylalanylamino)phenylthio)-1H-benzimidazol-2yl]carbamate used as starting material was prepared as follows:

A suspension of methyl [5(6)-(4-aminophenylthio)-1H-benzimidazol-2yl]carbamate (150 mg) in anhydrous tetrahydrofuran (4 ml) was treated with N-tert-butoxycarbonylalanine (100 mg), cooled to −35° C. and treated with 1-(3-dimethylaminopropyl)-3-ethylcarbodiimide (100 mg). The mixture was allowed to warm to room temperature and stir for 16 h. Water (40 ml) and ethyl acetate (20 ml) were added and the mixture extracted with four portions of ethyl acetate (50 ml each). The combined extracts were washed with brine (50 ml), dried (MgSO4) and concentrated under reduced pressure. The residue was purified on silica gel eluting with ethyl acetate to give methyl [5(6)-(4-(Nα-tert-butoxycarbonylalanylamino)phenylthio)-1H-benzimidazol-2yl]carbamate (258 mg) as a white solid m.p. 222–224° C. m/e 485 (M$^+$).

EXAMPLE 6

Methyl [5(6)-(4-(methoxycarbonylamino)phenylthio)-1H-benzimidazol-2yl]carbamate

Methyl [5(6)-(4-aminophenylthio)-1H-benzimidazol-2yl] carbamate(150 mg, 048 mmol) was dissolved in dimethylformamide (2 ml) and tetrahydrofuran (2 ml) and methyl chloroformate (40 mg, 0.42 mmol) added together with triethylamine (43 mg, 0.42 mmol). The solution was stirred at 20° C. for 72 h and then evaporated to dryness under reduced pressure. The residue was purified by chromatography on silica gel eluting with 5% methanol/dichloromethane to give the title compound as a white solid; mp >350° C. (dec.).

EXAMPLE 7

Methyl [5(6)-(4-(phenylaminocarbonylamino)phenylthio)-1H-benzimidazol-2yl]carbamate Methyl [5(6-(4-aminophenylthio)-1H-benzimidazol-2yl] carbamate (150 mg, 0.48 mmol) was dissolved in dimethylformamide (2 ml) and tetrahydrofuran (2 ml) and phenylisocyanate (56.8 mg, 0.48 mmol) added together with triethylanine (50 mg, ca. 0.5 mmol). The solution was stirred at 20° C. for 12 h and the solvents removed in vacuo. The residue was purified on silica (ethyl acetate/hexane, 2:1) to give the title compound as a white solid; mp 335–340° C. (dec.).m/e 433 ($M^+$).

EXAMPLE 8

Methyl [5(6)-(4-(methoxycarbonyloxy)benzoyl)-1H-benzimidazol-2yl]carbamate

Methyl [5(6)-(4-hydroxybenzoyl)-1H-benzimidazol-2yl] carbamate (110 mg, 0.35 mmol) was dissolved in dimethylformamide (3.5 ml) and triethylamine (0.5 ml). The solution was cooled to 0° C. and methyl chloroformate (50 mg, 0.52 mmol) added with stirring. The solution was stirred for 0.5 h at 0° C. and the 1 h at 20° C. and evaporated to dryness. The residue was dissolved in ethyl acetate (50 ml) and washed with sodium bicarbonate (sat., aq., 50 ml) and brine (50 ml), dried and evaporated. The residue was purified by radial chromatography on silica gel eluting with ethyl acetate/hexane, 1:1 followed by ethyl acetate to give the title compound as a white solid; mp 224–226° C. (dec).m/e 369 ($M^+$).

Prepared in an analogous fashion to Example 1 were:

EXAMPLE 9

Methyl [5(6)-(2-methoxycarbonylphenylthio)-1H-benzimidazol-2yl]carbamate from methyl 2-(3,4-diaminophenylthio)benzoate (1.5 g) and 1,3-bis(methoxycarbonyl)-S-methyl isothiourea (2.25 g) there was obtained the title compound (1.51 g) as a white solid m.p. 228–230 m/e 357 (M+). Anal. Calculated for $C_{17}H_{15}N_3O_4S$: C, 57.13; H, 4.23;N, 11.75. Found: C, 57.39; H, 4.13; N, 11.1.

EXAMPLE 10

Methyl [5(6)-(3-methoxycarbonylphenylthio)-1H-benzimidazol-2yl]carbamate from methyl 3-(3,4-diaminophenylthio)benzoate (246 mg) and 1,3-bis(methoxycarbonyl)-S-methyl isothiourea (371 mg) there was obtained the title compound (183 mg) as an off-white solid m.p. 226–228 m/e 357 (M+). Anal. Calculated for $C_{17}H_{15}N_3O_4S$: C, 57.13; H, 4.23; N, 11.75. Found: C, 56.58; H, 4.31; N, 11.86.

EXAMPLE 11

Methyl [5(6)-(4-methoxycarbonylphenylthio)-1H-benzimidazol-2yl]carbamate from methyl 4-(3,4-diaminophenylthio)benzoate (830 mg) and 1,3-bis(methoxycarbonyl)-S-methyl isothiourea (1.25 g) there was obtained the title compound (694 mg) as an off-white solid m.p. 280–282 m/e 357 (M+). Anal. Calculated for $C_{17}H_{15}N_3O_4S$: C, 57.13; H, 4.23; N, 11.75. Found: C, 57.21; H, 4.31; N, 11.73.

EXAMPLE 12

Methyl [5(6)-(4-hydroxyphenylthio)-1H-benzimidazol-2yl]carbamate from 4-(4-hydroxyphenylthio)-1,2-phenylenediamine (4 g) and 1,3-bis(methoxycarbonyl)-S-methyl isothiourea (6 g) there was obtained the title compound (2.4 g) as a white solid m.p. 202–204° C. m/e 315 ($M^+$). $^1$H-NMR (400 MHz, d6-DMSO) δ 3.74 (s, 3H), 6.76 and 7.2 (AA'BB', 4H, J=8.6 Hz), 7.03 (dd, 1H J=1.7, 6.6 Hz,), 7.29 (d, 1H, J=1.4 Hz,), 7.34 (d, 1H, J=8.3 Hz,), 9.68 (b, 1H,), 11.67 (b, 2H) ppm.

EXAMPLE 13

Methyl [5(6)-(4-(acetylamino)phenoxy)-1H-benzimidazol-2yl]carbamate from 4-(4-(acetylamino)phenoxy)-1,2-phenylenediamine (1.02 g) and 1,3-bis(methoxycarbonyl)-S-methyl isothiourea (2.67 g) there was obtained the title compound (0.93 g) as a white solid m.p. 304–306° C. m/e 340 ($M^+$). Anal. Calculated for $C_{17}H_{16}N_4O_4$: C, 60.00; H, 4.74; N, 16.46. Found: C, 60.03; H, 4.72; N, 16.42.

Prepared in an analogous fashion to Example 3 was:

EXAMPLE 14

Methyl [5(6)-(4-phosphonooxyphenoxy)-1H-benzimidazol-2yl]carbamate from methyl [5(6)-(4-(di-tert-butylphosphonooxy)phenoxy)-1H-benzimidazol-2yl]carbamate (200 mg) there was obtained the title compound (140 mg) as a white solid m.p. 272–275° C.

EXAMPLE 15

Methyl [5(6)-(4-hydroxy-α-hydroxyiminobenzyl)-1H-benzimidazol-2yl]carbamate

[5(6)-(4-hydroxybenzoyl)-1H-benzimidazol-2yl]carbamate (100 mg, 0.32 mmol) was added to a solution of hydroxylamine (0.8 mmol) in MeOH (20 mL, prepared by treatment of hydroxylamine hydrochloride (0.64 g, 1.6 mmol) and NaOH (0.14 g, 1.6 mmol) followed by filtration). The solution was heated at 70° C. for 36 h, cooled and water (30 ml) added. The solution was filtered and washed with ether and the solid triturated with methanol to yield the title compound (40 mg) as a white solid; mp 288–290° C.

The following known compounds were prepared by literature methods:

EXAMPLE 16

Methyl [5(6)-(4-(acetylamino)phenoxy)-1H-benzimidazol-2yl]carbamate

EXAMPLE 17

Methyl [5(6)-(4-aminophenoxy)-1H-benzimidazol-2yl]carbamate

EXAMPLE 18

Methyl [5(6)-(3-aminophenoxy)-1H-benzimidazol-2yl]carbamate

EXAMPLE 19

[5(6)-(4-hydroxybenzoyl)-1H-benzimidazol-2yl] carbamate

EXAMPLE 20

[5(6)-(2-hydroxybenzoyl)-1H-benzimidazol-2yl] carbamate

EXAMPLE 21

[5(6)-(3-hydroxybenzoyl)-1H-benzimidazol-2yl] carbamate

The invention claimed is:

1. A method for treatment of a solid cancerous tumor in a mammal wherein a composition of formula I is administered to said mammal in a dosage sufficient to damage new vasculature but insufficient to exhibit anti-mitotic activity:

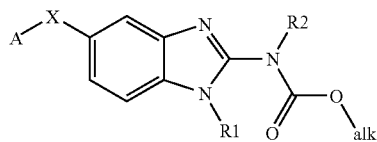

I wherein:
  alk is an alkyl group;
  X is oxygen, sulfur, sulphinyl, sulphonyl, carbonyl (CO), thiocarbonyl (CS), sulphonyloxy, NH, iminomethylene (C=NH), N-hydroxyiminomethylene, N-alkoxyiminomethylene, dialkoxymethylene, 1,3-dioxolan-2yl, 1,1-ethenyl, a group $CHR^3$ or a bond;
  $R^1$ is hydrogen, alkylaminocarbonyl or alkoxycarbonyl;
  $R^2$ is hydrogen, alkoxycarbonyl, cyanomethyl, cyanoethyl, alkoxymethyl or acetoxymethyl;
  $R^3$ is hydrogen, hydroxy, alkoxy or amino;
  A is a substituted aromatic or substituted alkyl group; wherein the substituent on A is selected from phosphate, alkylphosphate, $NHC(O)R^4$, $NR^5C(O)R^4$,
  $R^4$ and $R^5$, which may be the same or different, are each an alkyl group substituted with one or more substituents selected from hydroxy, amino, alkylamino, guanidino, carboxyl, $SO_3H$, sulfate and phosphate; and
  prodrugs and pharmaceutically acceptable salts, solvates and hydrates thereof.

2. The method of claim 1 wherein said composition is administered in the range of about 0.001 to about 100 mg/kg body weight.

3. The method of claim 1 wherein said composition is administered in the range of about 0.1 to about 50 mg/kg body weight.

4. A method according to claim 1 further comprising the simultaneous or sequential administration of one or more of a mitotic inhibitor, an alkylating agent, an antimetabolite, an intercalating agent, an enzyme, a topoisomerase inhibitor, a thymidylate synthase inhibitor, a biological response modifier, an antibody, an anti-hormone, or any combination thereof.

5. A method according to claim 4 wherein said mitotic inhibitor comprises at least one of vinblastine, paclitaxel, docetaxel, or any combination thereof.

6. A method according to claim 4 wherein said alkylating agent comprises at least one of cisplatin, carboplatin, cyclophosphamide, or any combination thereof.

7. A method according to claim 4 wherein said antimetabolite comprises at least one of 5-fluorouracil, cytosine arabinoside, hydroxyurea, or any combination thereof.

8. A method according to claim 4 wherein said intercalating agent comprises at least one of adriamycin, bleomycin, or any combination thereof.

9. A method according to claim 4 wherein said enzyme comprises aspariginase.

10. A method according to claim 4 wherein said topoisomerase inhibitor comprises at least one of etoposide, topotecan, irinotecan, or any combination thereof.

11. A method according to claim 4 wherein said thymidylate synthase inhibitor comprises raltitrexed.

12. A method according to claim 4 wherein said biological response modifier comprises interferon.

13. A method according to claim 4 wherein said antibody comprises at least one of edrecolomab and antibodies against the EGFr, HER2 receptor or VEGF receptor, or any combination thereof.

14. A method according to claim 4 wherein said anti-hormone comprises tamoxifen.

* * * * *